United States Patent [19]

Deger et al.

[11] Patent Number: 5,278,081
[45] Date of Patent: Jan. 11, 1994

[54] METHOD FOR THE DETERMINATION OF AN IMMUNOLOGICALLY BINDABLE SUBSTANCE

[75] Inventors: Arno Deger, Seeshaupt; Wolfgang Uhl, Weilheim, both of Fed. Rep. of Germany

[73] Assignee: Boehringer Mannheim GmbH, Mannheim, Fed. Rep. of Germany

[21] Appl. No.: 968,139

[22] Filed: Oct. 29, 1992

[30] Foreign Application Priority Data

Oct. 31, 1991 [DE] Fed. Rep. of Germany ....... 4136010

[51] Int. Cl.$^5$ ................ G01N 33/543; G01N 33/537; G01N 33/53
[52] U.S. Cl. .................................. 436/518; 436/512; 436/825; 435/7.5; 435/7.92; 435/7.94; 435/969; 435/962; 435/975
[58] Field of Search ..................... 435/7.5, 7.92, 7.94, 435/969, 962, 975; 436/512, 518, 825

[56] References Cited

U.S. PATENT DOCUMENTS 4,870,007 9/1989 Smith-Lewis ........................ 435/28

OTHER PUBLICATIONS

Odell et al, Clin. Chem., vol. 32, No. 10, pp. 1873-1878 (1986), "Two-Monoclonal-Antibody Sandwich-Type Assay for Thyrotropin, with Use of an Avidin-Biotin Separation Technique".

*Primary Examiner*—Toni R. Scheiner
*Attorney, Agent, or Firm*—Nikaido, Marmelstein, Murray & Oram

[57] ABSTRACT

In order to determine an analyte by a heterogeneous immunological test using a first partner of a binding pair which is immobilized on a solid phase in which a sample solution containing the analyte is incubated in the presence of the solid phase with either (1) a first conjugate consisting of (a) the second partner of the above-mentioned binding pair and (b) a first substance capable of specific immunological binding to the analyte or (2) a first conjugate consisting of (a) the second partner of the above-mentioned binding pair and (b) a first substance capable of specific immunological binding to the analyte as well as with a second labelled substance capable of specific immunological binding to the analyte, afterwards the phases are separated, in case (1) the liquid phase is replaced by a further solution containing a second labelled substance capable of binding specifically to the analyte and it is again incubated and subsequently separated, and in both cases the label on the solid phase or in the liquid phase which was separated last is measured as a measure of the amount of analyte, a second conjugate of (a) a macromolecule which is not capable of binding to the analyte and (b) the second partner of the above-mentioned binding pair is additionally added to the liquid phase in excess over the first conjugate before the incubation.

16 Claims, No Drawings

METHOD FOR THE DETERMINATION OF AN IMMUNOLOGICALLY BINDABLE SUBSTANCE

DESCRIPTION

The invention concerns a method for the determination of an immunologically bindable substance.

The utilization of the high binding strength between streptavidin and biotin for constructing immunological test procedures has already been realized in a multitude of forms. Streptavidin immobilized on an inert material (polystyrene beads, tubes etc.) serves as a universal solid phase with a high binding capacity for the corresponding biotinylated reagent. Coating methods which are readily reproducible and the excellent stabilities of the streptavidin matrix form the basis for the high precisions which can be achieved with this technology.

Despite the described high quality of streptavidin solid phases, one cannot completely rule out the possibility of inhomogeneity and interferences in particular the so-called "leaching effects" caused by detachment of streptavidin bound to the solid phase from the membrane. Tests which are particularly sensitive can react to this with a significant impairment of performance. The disadvantages compared to directly coated carriers are particularly marked in 1-step sandwich assays with only one antibody forming the basis for the capture and marker components. The stoichiometry which has to be selected for the two immunological reagents represents a concentration ratio which is finely matched to the reactions proceeding in the test mixture. "Plateau regions" do not always exist for the biotinylated component which can compensate for interferences of a small magnitude. Consequently problems with stability and production variations have to be rated as critical in these cases.

The object of the present invention was therefore to provide a method in which the test result is not influenced by such leaching effects.

This object is achieved according to the present invention by a method for the determination of an analyte by a heterogeneous immunological test using a first partner of a binding pair which is immobilized on a solid phase in which a sample solution containing the analyte is incubated in the presence of the solid phase with either (1) a first conjugate consisting of (a) the second partner of the above-mentioned binding pair and (b) a first substance capable of specific immunological binding to the analyte, or 2) a first conjugate consisting of (a) the second partner of the above-mentioned binding pair and (b) a first substance capable of specific immunological binding with the analyte as well as to a second labelled substance capable of specific immunological binding to the analyte, afterwards the phases are separated, in case (1) the liquid phase is replaced by a further solution containing a second labelled substance capable of binding specifically to the analyte and it is again incubated and subsequently separated, and in both cases the label on the solid phase or in the liquid phase which was separated last is measured as a measure of the amount of analyte which is characterized in that before the incubation a second conjugate of (a) a macromolecule which is not capable of binding to the analyte and (b) the second partner of the above-mentioned binding pair is additionally added to the liquid phase in excess over the first conjugate.

Thus for the method according to the present invention heterologous immunoassays are suitable in which firstly the actual immune reaction between analyte and the first conjugate takes place, then the complex of analyte and immunologically specifically bindable substance which is formed in this process is immobilized on a solid phase and finally, after separating the liquid phase from the solid phase, a new liquid phase is added which then enables the detection of the analyte by means of the label of a second analyte-specific substance which is contained therein (case 1). However, it also enables a heterologous procedure to be carried out in which the first liquid phase contains the conjugate consisting of (a) the first substance capable of specific immunological binding to the analyte and (b) the partner capable of binding to the solid phase as well as the second labelled substance capable of specific immunological binding (case 2). In this process the analyte in a liquid phase is concomitantly labelled and bound to the solid phase and can then be determined directly in an immobilized state after removing excess label with the liquid phase.

By adding a second conjugate according to the present invention which consists of (a) a macromolecule which is not capable of binding to the analyte and (b) a substance which is capable of binding to the solid phase the solid phase binding partners which become detached from the solid phase by leaching are neutralized and cannot interfere with the course of the immunological determination. Within the scope of the invention it surprisingly additionally turned out that a considerably improved quality of the calibration curve and thus of the sensitivity can be observed. An only very slight increase in signal for the lowest standard (10 to 20 mA) is in contrast to an absorbance increase of about 500 mA for the highest standard. A particular advantage of this is that it is associated with an optimization of the ability to differentiate in the very low concentration range. The general increase in the slope of the calibration curve with the same precision of the signal inevitably leads to lower concentration coefficients of variation. This may be due to the fact that solid phase partners which have previously become detached are bound again to the solid phase via the second conjugate which preferably has several binding sites for the solid phase partner. Conjugates with several binding sites for the solid phase partner are produced by reacting the macromolecule with the other binding partner in a molar excess of the binding partner, preferably of 5:1 to 10:1.

Again it surprisingly turns out that even at the level of the signal the coefficient of variation is decreased by ca. 50% which is presumably the result of the stronger saturation of the solid phase wall.

Within the scope of the method according to the present invention an antibody or even an antibody fragment is preferably used as the immunologically bindable substance. Monoclonal antibodies or fragments thereof (e.g. F(ab')$_2$, Fab or Fab' fragments) are preferably used for the method according to the present invention. A polyclonal antiserum can, however, also be used.

The specific binding pair used within the scope of the present invention is preferably biotin/streptavidin of which the streptavidin is in turn preferably bound to the solid phase and biotin is preferably bound to the substances present in the homogeneous phase i.e. to the specifically bindable substance as well as to the unspecific substance. According to the present invention a binding pair consisting of hapten/specific antibody can also for instance be used whereby digoxin is preferably used as the hapten.

The method according to the present invention makes it possible to prevent a reduction of the biotin present in the liquid phase which is caused by streptavidin which has become detached from the solid phase which neutralizes marked amounts of biotinylated substance which can bind specifically to the analyte. The procedure according to the present invention can be applied to all immunological tests in which ultimately the analyte is bound to the solid phase by means of a specific binding pair in heterologous immunoassays.

The conjugate of macromolecule and second partner of the binding pair used within the scope of the invention can preferably be a conjugate which contains a protein as the macromolecule that can, if desired, be modified by sugar, phosphate or/and lipid residues, e.g. an unspecific antibody i.e. an antibody (MW ca. 150000) which does not exhibit specific binding to any component of the test system or another protein such as albumins (MW 68000) like bovine serum albumin or aggregated albumin (MW>1 million, cf. EP-A 0 269 092). Further suitable macromolecules are e.g. carbohydrates, lipids, synthetic polymers and nucleic acids. The molecular weight of the macromolecules is preferably in the range from 50000 to 2 million. The production of the conjugates according to the present invention is carried out in a known manner preferably by reacting the activated binding partner (e.g. a reactive biotin derivative or a reactive hapten derivative e.g. digoxin derivative) with reactive groups (e.g. $NH_2$ or SH groups) on the macromolecule. The production of reactive biotin and hapten derivatives is described in JACS 100 (1978), 3585–3590.

The invention also concerns a reagent for determining an analyte by a heterogeneous immunological test using a first partner of a binding pair immobilized on a solid phase containing a first conjugate consisting of (a) the second partner of the above-mentioned binding pair and (b) a first substance capable of specific immunological binding to the analyte as well as a second labelled substance capable of specific immunological binding to the analyte, which is characterized in that it contains a second conjugate consisting of (a) a macromolecule which is not capable of binding to the analyte and (b) the second partner of the above-mentioned binding pair.

The second conjugate contained in the reagent according to the present invention consisting of (a) a macromolecule which is not capable of binding to the analyte and (b) the second partner of the binding pair is preferably a conjugate that has several binding sites for the first partner of the binding pair which is immobilized on the solid phase.

Streptavidin/biotin is preferably used as the binding pair in the reagent according to the present invention. The macromolecule contained in the reagent according to the present invention is preferably a protein, particularly preferably an unspecific antibody or bovine serum albumin.

In addition it is also preferred that in the reagent according to the present invention the second conjugate consisting of (a) a macromolecule which is not capable of binding to the analyte and (b) the second partner of the binding pair has several binding sites for the first partner of the binding pair.

The monoclonal antibody against creatine kinase of the MM type used in the examples was deposited at the European Collection of Animal Cell Cultures (ECACC), Porton Down, GB-Salisbury, Wiltshire SP4 OJG under the depositary number ECACC 88091404.

The following examples are intended to further elucidate the invention.

| Abbreviations: | |
|---|---|
| CK MM: | creatine kinase of the MM type |
| BSA: | bovine serum albumin |
| PEG 40000: | polyethylene glycol (MW:40000) |
| B-IgG: | bovine immunoglobulin G |

The stated percentages are percentages by weight.

EXAMPLE 1

Biotinylation of antibodies

Monoclonal antibodies against CK MM (ECACC 88091404) or against CA 125 (Boehringer Mannheim GmbH, Catalogue No. 11 22 789) are reacted with D-biotinyl-ε-aminocaproic acid-N-hydroxysuccinimide ester in a ratio of 7:1 (biotin: IgG) according to JACS 100 (1978) 3585–3590.

EXAMPLE 2

Biotinylation of bovine serum albumin (BSA) to form BSA biotin

For the biotinylation, BSA is reacted with D-biotinyl-ε-aminocaproic acid-N-hydroxysuccinimide ester in a ratio of 1:5 or 1:10 (BSA:biotin) according to JACS 100 (1978), 3585–3590.

EXAMPLE 3

Determination of CA 125 (one-step procedure)

10 μg/ml biotinylated MAB against CA 125 produced according to example 1, or if desired, 50 μg/ml biotinylated MAB against CKMM or 20–50 μg/ml biotinylated BSA (example 2) as well as a conjugate of peroxidase and MAB against CA 125 (peroxidase activity ca. 30 U/ml) are mixed with incubation buffer in a ratio of 1:1:1:100 to form the working solution.

| Incubation buffer (pH 7.4): | |
|---|---|
| Substance | Concentration |
| Na phosphate | 40 mmol/l |
| Di-Na tartrate | 200 mmol/l |
| Pluronic ® F 68 | 0.6% |
| Phenol | 0.01% |
| BSA | 0.2% |
| PEG 40000 | 0.75% |
| B-IgG | 0.1% |
| Washing solution: | 250 mg NaCl and 1 mg $CuSO_4$ in 1 l distilled $H_2O$ |

100 μl sample is incubated for 180 min with 1000 μl working solution in polystyrene tubes coated with streptavidin (prepared according to EP-A 0 269 092). The tubes are aspirated and washed twice with washing solution. Subsequently 1 ml substrate solution (100 mmol/l phosphate-citrate buffer pH 5.0, 1.47 mmol/l sodium perborate, 9.1 mmol/l 2,2'-azino-di-[3-ethyl-benzthiazoline sulfonic acid(6)] diammonium salt) is added, incubated for 60 min and the colour formed is determined photometrically at 420 nm. The results can be seen in Tables I to VII.

Legend for Tables:

MAB CK-Bi: Conjugate of MAB against CK MM with biotin (unspecific conjugate)
MAB CA 125-Bi: Conjugate of MAB against CA 125 with biotin (analyte-binding conjugate)
a–e: CA 125 standards concentrations from ca. 0–500 U/ml The numerical values in the tables are in each case absorbance values measured at 420 nm in mA (Table VII:E).

The effect of the increase in the signal intensity caused by the presence of the unspecific conjugate MAB CK-Bi is also found when the concentrations of the analyte-specific conjugate MAB CA 125-Bi are varied. The effect is particularly marked when MAB CK-Bi is present in excess.

TABLE III

Broadening of the measurement plateau by addition of MAB CK-Bi in a constant ratio to MAB CA 125-Bi

| MAB CA 125-Bi [μg/ml] | 0,05 | 0,06 | 0,07 | 0,08 | 0,09 | 0,10 | 0,12 | 0,14 | 0,15 | 0,16 | 0,18 | 0,20 |
|---|---|---|---|---|---|---|---|---|---|---|---|---|
| MAB CK-Bi [μg/ml] | 0,25 | 0,30 | 0,35 | 0,40 | 0,45 | 0,50 | 0,60 | 0,70 | 0,75 | 0,80 | 0,90 | 1,0 |
| a | 180 | 170 | 190 | 180 | 180 | 170 | 160 | 170 | 170 | 160 | 170 | 170 |
| b | 410 | 400 | 410 | 420 | 420 | 410 | 410 | 400 | 380 | 380 | 370 | 370 |
| c | 1050 | 1030 | 1070 | 1070 | 1050 | 1070 | 1010 | 1010 | 1000 | 980 | 900 | 690 |
| d | 1920 | 1930 | 2010 | 1990 | 1990 | 1940 | 1900 | 1860 | 1840 | 1800 | 1710 | 1590 |
| e | 2760 | 2810 | 2870 | 2860 | 2840 | 2810 | 2820 | 2730 | 2670 | 2600 | 2480 | 2360 |

Addition of the unspecific conjugate MAB CK-Bi according to the present invention in a molar excess of 5:1 in relation to the analyte binding conjugate MAB CA 125-Bi results in a broader measurement plateau for the concentration of MAB CA125-Bi.

TABLE IV

Precision within series without addition of MAB CK-Bi, MAB CA 125-Bi: 0.1 μg/ml

| | 20 individual determinations | | |
|---|---|---|---|
| | Standard solution | Human serum 1 | Human serum 2 |
| x | 7.02 U/ml | 10.21 U/ml | 18.14 U/ml |
| s | 4.50 U/ml | 4.67 U/ml | 4.46 U/ml |
| $V_k$ | 64% | 46% | 25% |

TABLE 1

Effect of varying the amount of MAB CK-Bi added on the slope of the calibration curve concentration of MAB CA 125-Bi: 0.2 μg/ml

| MAB CK-Bi [μg/ml] | 0 | 0,05 | 0,10 | 0,15 | 0,20 | 0,25 | 0,30 | 0,35 | 0,40 | 0,45 | 0,50 |
|---|---|---|---|---|---|---|---|---|---|---|---|
| a | 160 | 150 | 160 | 150 | 150 | 160 | 170 | 160 | 180 | 180 | 190 |
| b | 330 | 360 | 360 | 350 | 320 | 350 | 360 | 390 | 360 | 400 | 390 |
| c | 760 | 800 | 830 | 800 | 830 | 890 | 880 | 890 | 910 | 930 | 980 |
| d | 1510 | 1430 | 1620 | 1510 | 1530 | 1660 | 1730 | 1620 | 1580 | 1640 | 1720 |
| e | 2080 | 2180 | 2180 | 2240 | 2270 | 2390 | 2460 | 2370 | 2430 | 2380 | 2540 |

It can be seen from Table 1 that when the conjugate MAB CK-Bi that is not capable of binding to the analyte is added in excess over the test conjugate MAB CA125-Bi the signal intensity is surprisingly significantly higher than in the absence of the conjugate MAB CK-Bi.

TABLE II

Influence of varying concentrations of MAB CA 125-Bi with and without the addition of MAB CK-Bi

| MAB CA 125-Bi [μg/ml] | 0.05 | 0.10 | 0.20 | 0.30 | 0.40 | 0.50 | 1.00 |
|---|---|---|---|---|---|---|---|
| a) without MAB CK-Bi | | | | | | | |
| a | 160 | 160 | 150 | 120 | 110 | 90 | 70 |
| b | 360 | 350 | 310 | 270 | 240 | 180 | 110 |
| c | 860 | 890 | 790 | 660 | 570 | 500 | 320 |
| d | 1520 | 1670 | 1500 | 1230 | 1090 | 940 | 570 |
| e | 2290 | 2450 | 2220 | 1850 | 1590 | 1320 | 720 |
| b) with MAB CK-Bi (0.5 μg/ml) | | | | | | | |
| a | 190 | 170 | 150 | 140 | 130 | 110 | 80 |
| b | 440 | 420 | 360 | 290 | 260 | 220 | 150 |
| c | 1090 | 1090 | 910 | 730 | 620 | 530 | 380 |
| d | 1980 | 1970 | 1660 | 1400 | 1150 | 980 | 590 |
| e | 2880 | 2940 | 2410 | 2030 | 1700 | 1450 | 860 |

TABLE V

Precision within series 0.1 μg/ml MAB CA 125-Bi (degree of biotinylation 1:10) with addition of 0.5 μg/ml MAB CK-Bi

| | 20 individual determinations | | |
|---|---|---|---|
| | Standard solution | Human serum 1 | Human serum 2 |
| x | 4.92 U/ml | 6.83 U/ml | 12.34 U/ml |
| s | 1.90 U/ml | 2.11 U/ml | 1.26 U/ml |
| $V_k$ | 39% | 31% | 10% |

A comparison of tables IV and V shows that precision of the determination of antigen CA-125 is increased by addition of the unspecific conjugate MAB CK-Bi.
x: mean of 20 determinations
s: standard deviation
$V_k$: coefficient of variation based on concentration

TABLE VI

Influence of different concentrations of the unspecific conjugate BSA-biotin (degree of biotinylation 1:5 or 1:10) in the CA 125 test on the signals of the calibration curve.

| CA 125-Bi [μg/ml] | 0,15 | | | | | 0,1 | | | | | 0,2 | | | | | 0,4 | | | | |
|---|---|---|---|---|---|---|---|---|---|---|---|---|---|---|---|---|---|---|---|---|
| BSA biotin [μg/ml] | 0 | 0,2 | 0,5 | 0,7 | 1,0 | 0,1 | 0,2 | 0,5 | 0,7 | 1,0 | 0,1 | 0,2 | 0,5 | 0,7 | 1,0 | 0,1 | 0,2 | 0,5 | 0,7 | 1,0 |
| 1:5  a | 150 | 120 | 90 | 110 | 90 | 110 | 110 | 130 | 140 | 110 | 120 | 140 | 160 | 150 | 140 | | | | | |

TABLE VI-continued

Influence of different concentrations of the unspecific conjugate BSA-biotin (degree of biotinylation 1:5 or 1:10) in the CA 125 test on the signals of the calibration curve.

| CA 125-Bi [µg/ml] | | 0,15 | | 0,1 | | | | | 0,2 | | | | | 0,4 | | | | |
|---|---|---|---|---|---|---|---|---|---|---|---|---|---|---|---|---|---|---|
| BSA biotin [µg/ml] | | 0 | 0,2 | 0,5 | 0,7 | 1,0 | 0,1 | 0,2 | 0,5 | 0,7 | 1,0 | 0,1 | 0,2 | 0,5 | 0,7 | 1,0 |
| | b | 300 | 320 | 300 | 300 | 280 | 300 | 290 | 270 | 290 | 260 | 260 | 280 | 280 | 240 | 250 |
| | c | 780 | 890 | 830 | 810 | 770 | 800 | 770 | 730 | 770 | 730 | 600 | 630 | 650 | 600 | 610 |
| | d | 1480 | 1630 | 1580 | 1580 | 1490 | 1510 | 1420 | 1430 | 1460 | 1420 | 1180 | 1160 | 1180 | 1120 | 1110 |
| | e | 1930 | 2140 | 2060 | 2090 | 1980 | 2000 | 1930 | 1890 | 1980 | 1900 | 1540 | 1580 | 1610 | 1490 | 1430 |
| 1:10 | a | 110 | 110 | 100 | 100 | 100 | 120 | 150 | 140 | 150 | 140 | 120 | 130 | 140 | 120 | 140 |
| | b | 320 | 360 | 340 | 280 | 250 | 300 | 300 | 300 | 320 | 270 | 280 | 270 | 260 | 250 | 240 |
| | c | 780 | 950 | 890 | 810 | 710 | 770 | 770 | 790 | 780 | 680 | 650 | 640 | 590 | 560 | |
| | d | 1470 | 1770 | 1700 | 1570 | 1360 | 1510 | 1560 | 1530 | 1410 | 1240 | 1200 | 1210 | 1160 | 1090 | 1070 |
| | e | 1840 | 2320 | 2270 | 2070 | 1830 | 2060 | 2100 | 2070 | 1980 | 1690 | 1530 | 1540 | 1540 | 1450 | 1420 |

TABLE VII

Within-series precision BSA-biotin is added

| | | without biotin conjugate | | | | +0,5 µg/ml BSA-biotin (1:10) | | | |
|---|---|---|---|---|---|---|---|---|---|
| | | Absorbance A | | U/ml | | Absorbance A | | U/ml | |
| Samples | | 10 DD | 20 SD | 10 DD | 20 SD | 10 DD | 20 SD | 10 DD | 20 SD |
| Standard a | x | 0,116 | 0,116 | 4,68 | 5,24 | 0,113 | 0,115 | 2,83 | 3,12 |
| | s | 0,005 | 0,006 | 2,58 | 2,15 | 0,004 | 0,005 | 0,96 | 1,38 |
| | $V_k$ | 5% | 5% | 55% | 41% | 3% | 4% | 34% | 44% |
| HS 1 | x | 0,160 | 0,160 | 19,24 | 19,22 | 0,162 | 0,161 | 14,34 | 14,44 |
| | s | 0,010 | 0,013 | 3,10 | 3,78 | 0,003 | 0,006 | 0,78 | 1,26 |
| | $V_k$ | 6% | 8% | 16% | 20% | 2% | 3% | 5% | 9% |
| HS 2 | x | 0,166 | 0,166 | 20,94 | 20,93 | 0,174 | 0,173 | 17,01 | 17,01 |
| | s | 0,010 | 0,011 | 3,04 | 3,33 | 0,003 | 0,008 | 0,64 | 1,73 |
| | $V_k$ | 6% | 7% | 15% | 16% | 2% | 4% | 4% | 10% |
| HS 3 | x | 0,161 | 0,162 | 19,56 | 20,0 | 0,166 | 0,166 | 15,25 | 15,25 |
| | s | 0,013 | 0,012 | 3,79 | 3,67 | 0,006 | 0,009 | 1,31 | 1,91 |
| | $V_k$ | 8% | 8% | 19% | 18% | 4% | 5% | 9% | 13% |
| HS 4 | x | 0,174 | 0,174 | 23,39 | 23,39 | 0,184 | 0,184 | 19,32 | 19,32 |
| | s | 0,011 | 0,011 | 3,07 | 3,24 | 0,004 | 0,006 | 0,92 | 1,41 |
| | $V_k$ | 6% | 6% | 13% | 14% | 2% | 4% | 5% | 7% |
| HS 5 | x | 0,194 | 0,194 | 29,0 | 29,0 | 0,209 | 0,209 | 24,77 | 24,79 |
| | s | 0,009 | 0,010 | 2,42 | 2,68 | 0,004 | 0,007 | 0,92 | 1,48 |
| | $V_k$ | 4% | 5% | 8% | 9% | 2% | 3% | 4% | 6% |

HS: human serum
DD: duplicate determination
SD: single determination

EXAMPLE 4

Determination of oestradiol

100 µl sample (human serum) is transferred to a polystyrene tube coated with streptavidin and 70 ng of a biotinylated anti-oestradiol antibody (polyclonal, produced according to G. Brown et al., in D. Catty (ed.), Antibodies, Vol. I, A practical approach, IRL-Press, Washington, 1988, 85; immunization with oestradiol (Boehringer Mannheim GmbH, Catalogue No. 11 22 789)) in 500 µl incubation buffer (100 mmol/l phosphate buffer pH 7.0) is added and incubated for 30 minutes.

After addition of a conjugate of peroxidase and anti-oestradiol antibody (Boehringer Mannheim GmbH, Catalogue No. 11 22 789, 150 mU/ml POD activity in 500 µl incubation buffer) it is incubated for a further 60 minutes. After aspirating the liquid phase and washing the tubes several times with washing solution, 1 ml substrate solution is added, incubated for 30 minutes and the colour formed is determined photometrically at 420 nm. The results can be seen in Table VIII.

TABLE VIII

| | Variant 1 | | Variant 2 | | Difference 2/1 |
|---|---|---|---|---|---|
| Sample | mA | % CV | mA | % CV | % |
| 1 | 243 | 8.3 | 302 | 6.6 | 20 |
| 2 | 112 | 8.7 | 158 | 3.4 | 61 |
| 3 | 34 | 13.8 | 59 | 7.0 | 49 |
| 4 | 128 | 5.9 | 147 | 3.7 | 37 |
| Mean | | 9.2 | | 5.2 | 44 |

Variant 1: 3 ng biotin/ml
Variant 2: 1.5 µg TBSA biotin (1:15)/ml
mA: absorbance at 420 nm in mA Table VIII shows that the addition of biotin alone is not suitable for significantly improving the precision of the test. Only the addition of a conjugate of high molecular BSA (TBSA, produced according to EP A 0 269 092) with biotin (TBSA-biotin) leads to an improvement of precision.

We claim:
1. A method for determination of an analyte by a heterogeneous immunoassay comprising:
   (i) incubating a sample solution containing the analyte with (a) a first partner of a binding pair immobilized on a solid phase, (b) a first conjugate consisting of a first substance which specifically immunologically binds the analyte conjugated to a second partner of said binding pair, and (c) a second conjugate comprising the second partner of said binding pair conjugated to a macromolecule which is not capable of binding to the analyte, wherein said second conjugate is present in excess over the first conjugate;

(ii) separating the solid phase of step (i) from the sample solution;

(iii) incubating the solid phase of step (ii) with a second substance conjugated to a label, to form a solid phase and a liquid phase, wherein said second substance specifically immunologically binds the analyte;

(iv) separating the solid phase of step (iii) from the liquid phase; and (v) determining the amount of label either on the solid phase or in the liquid phase as a measure of the amount of analyte in the sample solution.

2. A method for determination of an analyte by a heterogeneous immunoassay comprising:

(i) incubating a sample solution containing the analyte with (a) a first partner of a binding pair immobilized on a solid phase, (b) a first conjugate consisting of a first substance which specifically immunologically binds the analyte conjugated to a second partner of said binding pair, (c) a second conjugate comprising the second partner of said binding pair conjugated to a macromolecule which is not capable of binding to the analyte, wherein said second conjugate is present in excess over the first conjugate, and (d) a second substance conjugated to a label, to form a solid phase and a liquid phase, wherein said second substance specifically immunologically binds the analyte;

(ii) separating the solid phase of step (i) from the sample solution; and (iii) determining the amount of label either on the solid phase or in the sample solution as a measure of the amount of analyte in the sample solution.

3. The method of claim 1 wherein the first and second substances which specifically immunologically bind the analyte are antibodies or antibody fragments.

4. The method of claim 2 wherein the first and second substances which specifically immunologically bind the analyte are antibodies or antibody fragments.

5. The method of claim 1 wherein the first and second substances which specifically immunologically bind the analyte bind the analyte in the same way.

6. The method of claim 2 wherein the first and second substances which specifically immunologically bind the analyte bind the analyte in the same way.

7. The method of claim 1 wherein said second conjugate is present in an excess of 2 to 10 over the first conjugate.

8. The method of claim 2 wherein said second conjugate is present in an excess of 2 to 10 over the first conjugate.

9. The method of claim 1 wherein said second conjugate has more than one binding site for the first binding partner of the binding pair.

10. The method of claim 2 wherein said second conjugate has more than one binding site for the first binding partner of the binding pair.

11. The method of claim 9 wherein said second conjugate has 5 to 10 binding sites for the first binding partner of the binding pair.

12. The method of claim 10 wherein said second conjugate has 5 to 10 binding sites for the first binding partner of the binding pair.

13. A reagent for determination of an analyte by a heterogeneous immunoassay wherein a first partner of a binding pair is immobilized on solid phase, comprising:

(a) a first conjugate consisting of a first substance which specifically immunologically binds the analyte conjugated to a second partner of said binding pair;

(b) a second conjugate comprising the second partner of said binding pair conjugated to a macromolecule which is not capable of binding to the analyte; and (c) a second substance conjugated to a label, wherein said second substance specifically immunologically binds the analyte.

14. The reagent of claim 13 wherein the first and second substances which specifically immunologically bind the analyte are antibodies or antibody fragments.

15. The reagent of claim 13 wherein the first and second substances which specifically immunologically bind the analyte bind the analyte in the same way.

16. The reagent of claim 13 wherein said second conjugate has more than one binding site for the first binding partner of the binding pair.

* * * * *